United States Patent [19]

Floyd, Jr.

[11] Patent Number: 4,958,037
[45] Date of Patent: Sep. 18, 1990

[54] PRECURSORS AND SYNTHESIS OF METHYL-9-OXO-11APHA, 16-DIHYDROXY-16-VINYL-5-CIS-13-TRANS-PROSTADIENOATES

[75] Inventor: Middleton B. Floyd, Jr., Suffern, N.Y.

[73] Assignee: American Cyanamid Company, Stamford, Conn.

[21] Appl. No.: 185,621

[22] Filed: Apr. 25, 1988

Related U.S. Application Data

[62] Division of Ser. No. 760,023, Jul. 29, 1985, abandoned.

[51] Int. Cl.[5] ............... C07D 307/32; C07D 307/42; C07D 307/54
[52] U.S. Cl. .................. 549/476; 549/478; 549/492; 549/497; 549/501; 549/502
[58] Field of Search ............. 549/476, 497, 502, 501, 549/491, 478, 492

[56] References Cited

U.S. PATENT DOCUMENTS 4,076,732  2/1978  Floyd ........................... 560/121

Primary Examiner—Robert Gerstl
Attorney, Agent, or Firm—H. G. Jackson

[57] ABSTRACT

Novel precursors for the synthesis of methyl-9-oxo-11α,16-dihydroxy-16-vinyl-5-cis-13-trans prostadienoates having the formulae

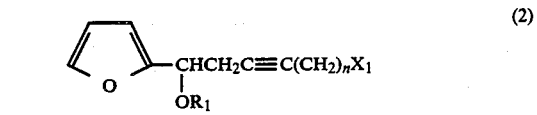

(2)

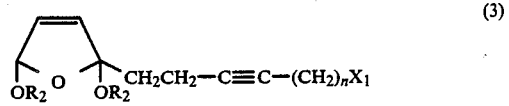

(3)

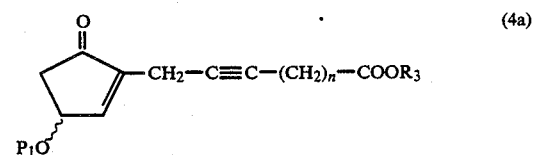

(4a)

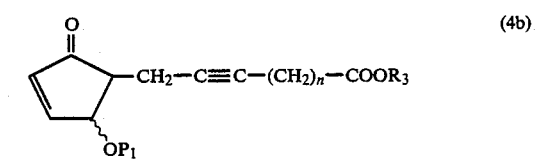

(4b)

wherein $R_1$ is H or $C_1$–$C_4$ alkyl; $R_2$ is $C_1$–$C_4$ alkyl, $R_3$ is H, $C_1$–$C_4$ trialkylsilyl or $C_1$–$C_6$ alkyl; $X_1$ is halogen, cyano, $C_1$–$C_4$ alkoxycarbonyl, carboxy or tri ($C_1$–$C_4$ alkoxy)methyl; n is 2–4 inclusive; and $P_1$ is H or a blocking or protective group; congeners and racemic mixture of these compounds and processes of synthesizing them.

9 Claims, No Drawings

PRECURSORS AND SYNTHESIS OF METHYL-9-OXO-11APHA, 16-DIHYDROXY-16-VINYL-5-CIS-13-TRANS-PROSTADIENOATES

This is a division of application, Ser. No. 760,023, filed July 29, 1985 now abandoned.

FIELD OF THE INVENTION

This invention relates to novel compounds which are advantageously used as precursors in the synthesis of methyl-9-oxo-11α,16-dihydroxy-16-vinyl-5-cis-13-transprostadienoates, their congeners and racemic mixtures thereof. These prostadienoates are pharmacologically active, for instance, as hypotensive agents and as vasodilators. One of such prostadienoates having vasodilator and hypotensive activity, namely methyl 9-oxo-11α, 16-dihydroxy-16-vinylprosta-5-cis-13-trans-dienoate, having the structure

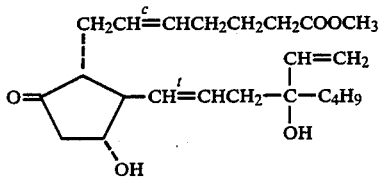

(1)

has been described in U.S. Pat. Nos. 4,198,521 and 4,311,707 and by J. E. Birnbaum, et al., J. Med. Chem., 25, 492 (1982).

This invention also relates to novel processes of synthesizing new compounds which are precursors to the pharmacologically active compounds cited above.

The novel compounds and processes of the invention provide a simpler, more rapid and economical means of producing pharmacologically active prostadienoates of greatly increased purity as compared to the compounds and processes used heretofore.

BRIEF SUMMARY OF THE INVENTION

The novel precursor compounds of this invention include the acetylenic furan derivatives represented by the

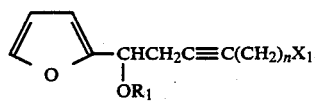

(2)

wherein $R_1$ is selected from the group consisting of hydrogen and $C_1$-$C_4$ alkyl; $X_1$ is selected from the group consisting of halogen, cyano, $C_1$-$C_4$ alkoxycarbonyl, carboxy and tri-($C_1$-$C_4$ alkoxy)methyl; and n is an integer 2–4 inclusive.

The novel precursor compounds also include the class of furan derivatives represented by the formula

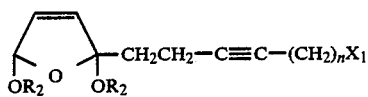

(3)

wherein $R_2$ is selected from the group consisting of $C_1$-$C_4$ alkyl and n and $X_1$ are as hereinabove defined.

From the compounds described hereinabove, one may obtain, by processes described below, additional novel compounds which are cyclopentenones of the class represented by the formulae

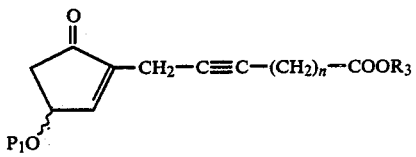

(4a)

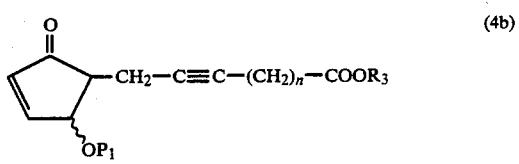

(4b)

wherein $R_3$ is a monovalent radical selected from the group consisting of hydrogen, $C_1$-$C_4$ trialkylsilyl and $C_1$-$C_6$ alkyl; n is an integer 2–4 inclusive; $P_1$ is a monovalent radical selected from the group consisting of hydrogen and $P_2$; and $P_2$ is a blocking or protective group which is stable under the conditions of the catalytic hydrogenation of the triple bond, as described hereinafter, or under the conditions of the 1,4 conjugate addition process to which compound (4a) is to be subjected, as described hereinafter, and which can thereafter be removed, usually by a mild acid treatment, without disruption of the prostaglandin product of which it forms a part. Such protective groups are well-known in the art and may be, for instance, tetrahydropyranyl, trialkylsilyl, such as trimethylsilyl or dimethyl-t-butylsilyl, or alpha-alkoxy ethyl.

It is significant that the novel intermediate of formula (4a), where P is H, n is 3 and $R_3$ is hydrogen, is crystalline. Its crystalline structure enhances and simplifies purification, thereby providing a more economical process of preparing a product of high purity.

Broadly described, the novel processes of this invention include the preparation of compounds of formula (2) by reacting an alkali metal acetylide of formula (5), wherein $R_4$ is $C_1$-$C_4$ alkyl or the alkali metal cation represented by M when M is a lithium, sodium or potassium cation; with a substituted alkyl bromide or iodide of formula (6)

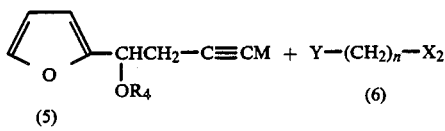

(5) (6)

wherein Y is bromo or iodo; n is an integer 2–4 inclusive and $X_2$ is selected from the group consisting of halogen and tri-($C_1$-$C_4$ alkoxy)methyl.

Alternatively the compound (7)

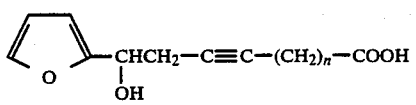

(7)

where n is an integer 2–4 inclusive, may be prepared by reacting 2-(2-furyl)oxirane [Zh. Organ.Khim., 1, 539 (1965)] with a di-(alkali metal)acetylide carboxylate (8)

(8)

where M and n are as defined hereinabove.

The novel processes also include the preparation of compounds of formula (3) by reacting an alkali metal acetylide (9)

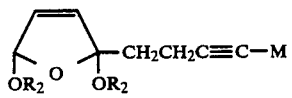

(9)

wherein $R_2$ and M are as defined hereinabove, with a substituted alkyl bromide or iodide defined by formula (6).

The compound of formula (2) or (3) is then subjected to an acid-catalyzed hydrolysis and isomerization, and, optionally, esterification, to form, via the intermediate 3-hydroxy isomer (4b), the 4-hydroxycyclopentenone compound (4a), wherein $P_1$ is hydrogen.

The 4-hydroxy group of the cyclopentenone is then protected (for subsequent reactions) with an appropriate blocking group $P_2$, as defined above.

The novel cyclopentenones (4a) are converted to the useful prostadienoates, most preferably, the compound of formula (1), by either of two routes.

In the first route the cyclopentenone alkynoate (4a) is subjected to partial catalytic hydrogenation to provide the cis-alkenoate (10)

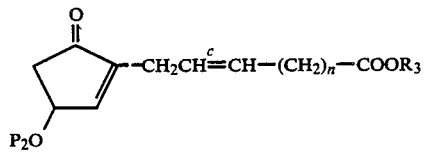

(10)

wherein $P_2$, n and $R_3$ are as defined hereinabove. This cyclopentenone (10), where n is 3 and $R_3$ is methyl, has been converted to the prostadienoate (1) by procedures described in J. Med. Chem., 25, 492 (1982).

In the second route, the cyclopentenone alkynoate (4a), where $P_1$ is $P_2$, is reacted with a lithio-cuprate reagent, or a functional equivalent thereof, which is capable of furnishing a prostaglandin beta-chain (11)

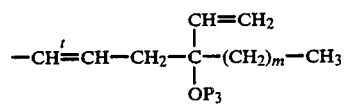

(11)

wherein m is an integer from 2–4 inclusive; and $P_3$ is a monovalent protective group with the same characteristics described above pertaining to $P_2$, and may be the same chemical moiety as, or may be different from, $P_2$.

A suitable lithio-cuprate reagent is disclosed in J. Med. Chem., 25, 492 (1982).

The product of the above reaction is a racemic and diastereomeric mixture of compounds (12)

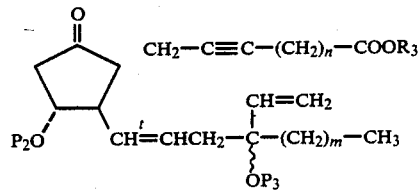

(12)

wherein m, n, $P_2$, $P_3$ and $R_3$ are as defined hereinabove.

The blocking groups $P_2$ and $P_3$ are then removed by hydrolysis to produce a mixture of diastereoisomers (13).

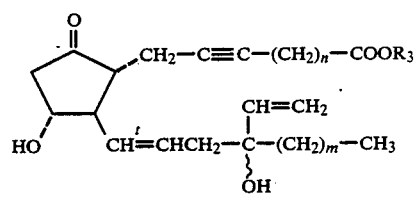

(13)

The triple bond of prostaglandin (13) is then subjected to partial catalytic hydrogenation to provide the prostadienoate (14).

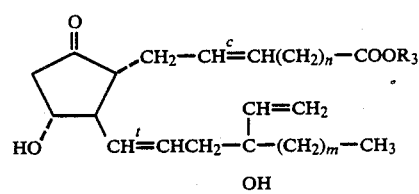

(14)

When n is 3, m is 3 and $R_3$ is methyl, the product of the foregoing comprises a racemic mixture corresponding to formula (1), a pharmaceutical agent with the properties described above.

The dotted lines shown in the above formulae indicate that the substituents are in the alpha configuration, i.e. below the plane of the cyclopentenoyl ring.

Many of the compounds described herein possess asymmetric centers and thus can be produced as racemic mixtures or as individual enantiomers. The racemic mixtures can be resolved at appropriate stages by methods known to those skilled in the art, to obtain the respective individual enantiomers. It is to be understood that the racemic mixtures and the individual enantiomers are encompassed within the scope of this invention.

A major advantage of the novel processes and products of the invention is the production of pharmacologically active prostadienoates with greatly enhanced purity which is directly attributable to the partial catalytic hydrogenation of the triple bonds of the compounds of formulae (4a), in the first route, which is preferred, or of formulae (13), in the second route. NMR analysis shows that whereas the methods practiced heretofore resulted in a product containing about 8–11% impurities, the novel processes and products of the instant invention produce a product with an impurity level of only about 1%. The major contaminants in the previous methods are compounds comprising the trans isomers of the pharmaceutically active prostadienoates, which contain negligible biological activity. By contrast, the partial catalytic hydrogenation of the triple bonds of the novel compounds of the invention is quite stereospecific, producing predominantly the much more biologically active cis stereoisomers without any additional purification procedures.

DETAILED DESCRIPTION

In the most preferred embodiment of the novel processes of the invention, the novel compounds of this invention are prepared as described in Flowchart A, wherein $R_5$ is $C_1$–$C_4$ alkyl and the substituents $R_1$, M, Y, n, $P_2$, $P_3$, and m are as described hereinabove.

FLOWCHART A

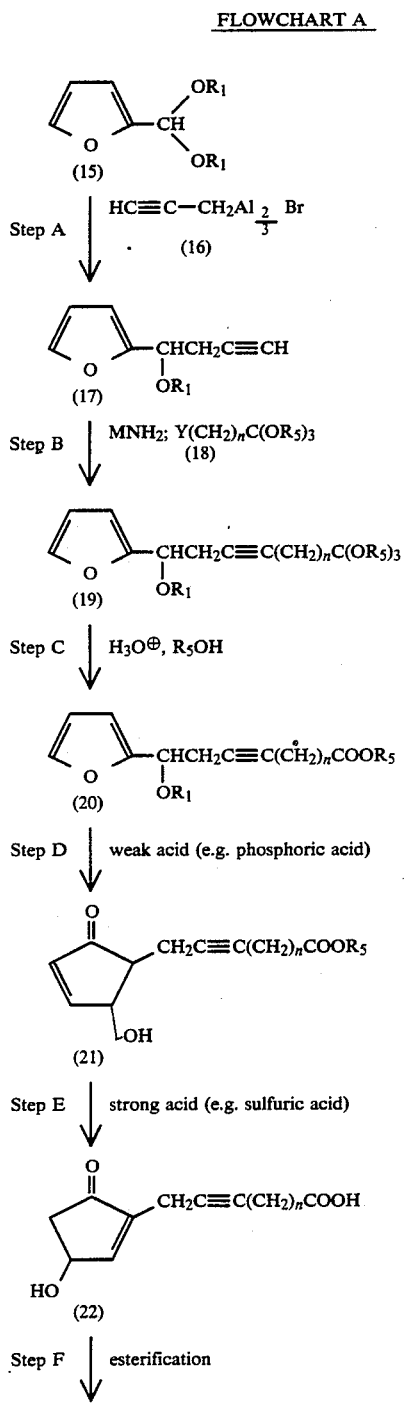

FLOWCHART A (continued)

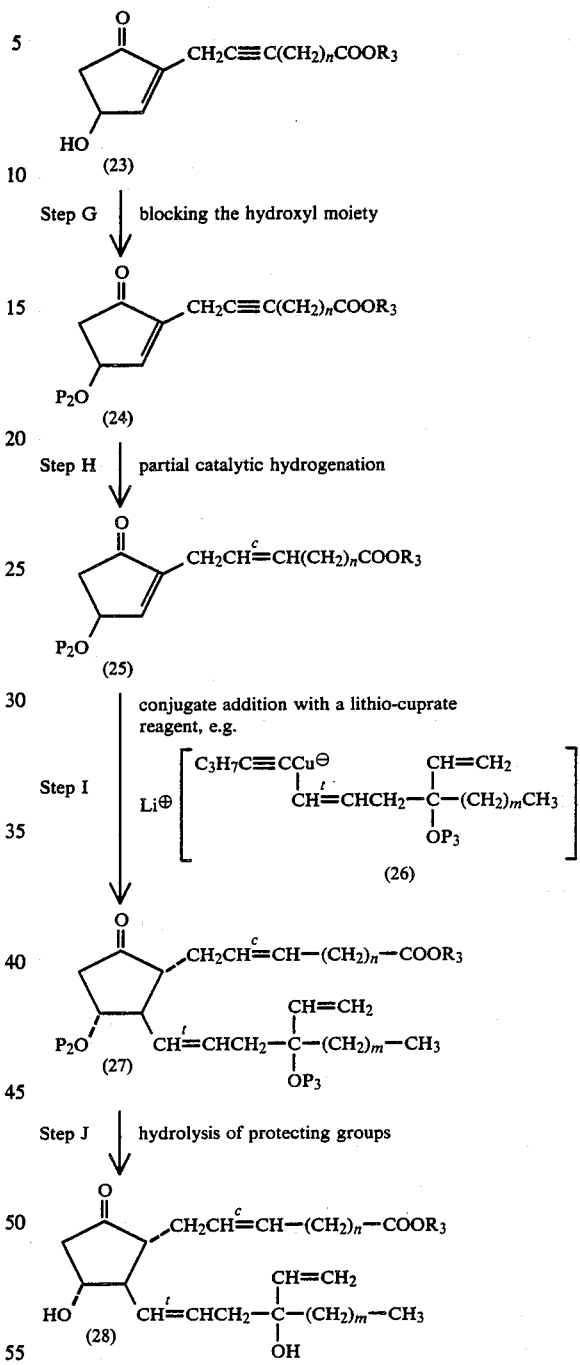

In accordance with the above flowchart A, a furfural dialkylacetal (15) is treated in step A with propargyl aluminum bromide (16) or its functional equivalent providing the ether (17). The metallation of the acetylene function in (17) is carried out preferably with an alkali metal amide in liquid ammonia. The preferred metal is lithium. The resulting species is not isolated but is reacted in step B with a bromide or iodide of formula (18) preferably in a cosolvent such as tetrahydrofuran and at $-35°$ to $+25°$ C. In the reactants of formula (18) the group $R_5$ in the orthoester function may be the same as or different from the group $R_3$ in formula (4a). The product of formula (19) is subjected in step C to mild acid hydrolysis in an alcohol solvent to provide the ester (20). The ester function may be hydrolyzed to the acid ($R_5$=H) under basic conditions, or optionally kept intact for the next stage, as shown in flowchart A.

The furylcarbinol ether (20) is then subjected in step D to a weak acid-catalyzed hydrolysis and rearrangement to a 3-hydroxycyclopentenone (21), usually present as a mixture with the 4-hydroxycyclopentenone isomer of (22). The reaction is accomplished with an aqueous organic solution of a weak organic acid such as formic acid, or alternatively with a phosphate buffer solution having a pH of about 1-3. The isomerization of the 3-hydroxy isomer (21) to the 4-hydroxy isomer (22) is completed in step E by the addition of a strong acid, such as sulfuric acid, to the solution of isomers, preferably in the same reaction zone.

The resulting carboxylic acid (22) is then esterified in step F, for instance by alkylation with an alkyl halide ($R_3$—X) such as iodomethane, or by controlled Fisher esterification, for example, with methanol.

The hydroxyl moiety of compound (23) is provided in step G with a protective group $P_2$ capable of subsequent removal under mild conditions, without effect on the rest of the molecule and capable of stability under the conditions of the partial catalytic hydrogenation or the conditions of the conjugate addition reaction. Advantageously, $P_2$ is trimethylsilyl or tetrahydropyranyl.

The partial catalytic hydrogenation, step H, of the triple bond in the compound (24) is preferably carried out with a poisoned palladium catalyst, or its equivalent, in a hydrocarbon solvent at $-10°$ to $+25°$ C. under one atmosphere of hydrogen The preferred catalyst is palladium on calcium carbonate, lead-poisoned (Lindlar catalyst).

The product cis-olefin (25) wherein $P_2$ is trimethylsilyl, n is 3 and $R_3$ is methyl, is a known intermediate for the preparation of the useful prostadienoate ester of formula (1). The requisite transformations which eventually provide the product (28) are depicted in steps I and J and are described in J. Med. Chem., 25, 492 (1982).

A major advantage of the above embodiment of the present invention, in addition to the high degree of stereo-selection in the conversion of the acetylene group to a cis-olefin group through the agency of controlled partial catalytic hydrogenation is the increased ease of purification of the crystalline compound (23), where n is 3 and $R_3$ is hydrogen, and the concomitantly decreased cost of preparation An alternative method for the preparation of prostadienoate esters such as (1) is shown in flowchart B, wherein $P_2$, n, $R_3$, $P_3$ and m are as hereinabove described.

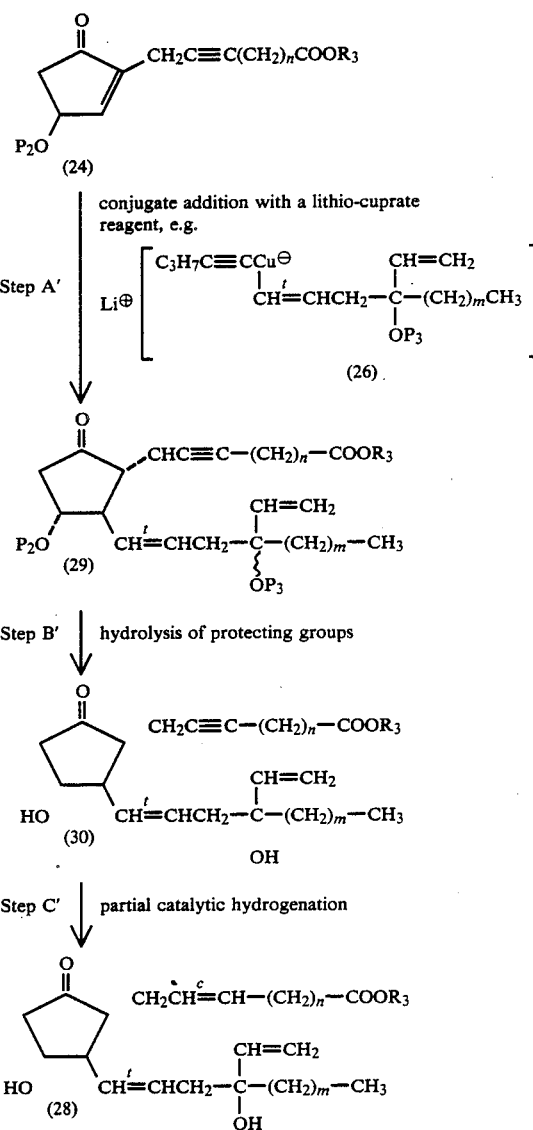

In accordance with flowchart B, the blocked cyclopentenone (24), prepared as described in flowchart A, is reacted in step A' with a lithio-cuprate reagent, preferably the reagent (26). The resulting blocked prostenynoate ester (29) is subjected to mild hydrolysis of the protecting groups $P_2$ and $P_3$ as shown in step B'. The preferred conditions employ acetic acid in aqueous tetrahydrofuran at 25°-40° C. The resulting acetylenic diol (30) is subjected to partial catalytic hydrogenation in step C' to provide the useful prostadienoate esters (28). The preferred conditions employ a hydrocarbon solvent at 25°-40°C. under one atmosphere of hydrogen. A useful catalyst is palladium on calcium carbonate, lead-poisoned (Lindlar catalyst).

Also included in the scope of this invention are alternative processes for the preparation of novel intermediate cyclopentenone alkynoates as shown in flowchart C, wherein n and M are as described hereinabove and $R_6$ is $C_1$-$C_4$ alkyl.

FLOWCHART C

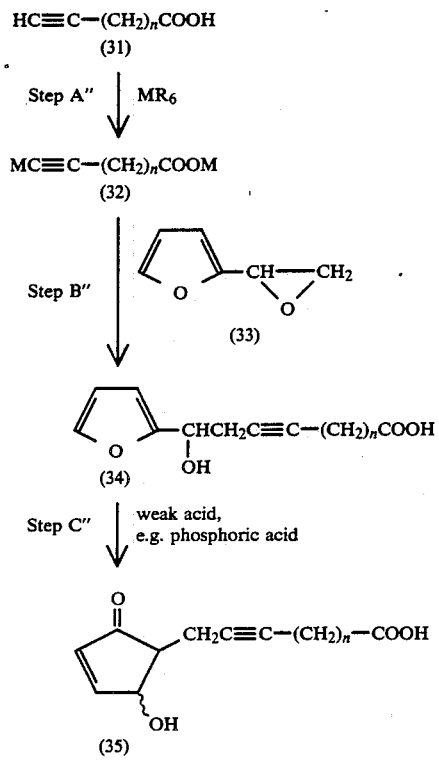

In accordance with flowchart C, treatment in step A''' of an ω-carboxy-1-alkyne (31) with a strong alkali metal base, preferably an alkyllithium, in a suitable solvent provides a dianionic species (32). The preferred solvent for this reaction is hexamethylphosphoramide. The intermediate (32) is not isolated but is reacted in step B'' with 2-(2-furyl)oxirane (33) to provide the hydroxy acid (34). The conversion of (34) to the cyclopentenone hydroxy acid isomer (35) is accomplished in step C'' using the method described in detail above for step D of flowchart A.

An additional novel route to the cyclopentenone alkynoates of this invention is shown in the following flowchart D, wherein n is as hereinabove defined.

FLOWCHART D

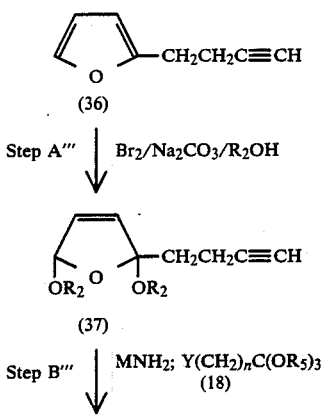

-continued
FLOWCHART D

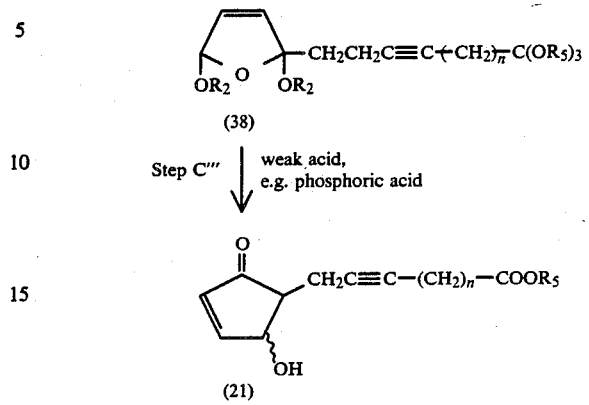

In accordance with flowchart D, 4-(2-furyl)-1-butyne (36) is reacted in step A''' with bromine and sodium carbonate in a lower alcohol solvent, preferably methanol. The dialkoxydihydrofuran (37) is treated in step B''' with an alkali metal amide, preferably lithium amide, in liquid ammonia. The resulting acetylide salt is not isolated but is reacted with a bromide or iodide (18), preferably in a cosolvent such as tetrahydrofuran at −35° to +25° C. The dialkoxydihydrofuran (38) is then subjected in step C''' by a weak acid-catalyzed hydrolysis and rearrangement to the 3-hydroxycyclopentenone alkynoate (21). The group $R_5$ in the orthoester and ester functions of (38) and (21) respectively may be the same or different from the group $R_3$ present in (24) of flowchart A. The preferred conditions for the reaction of step C''' employ a phosphate buffer solution in an aqueous organic solvent having a pH of about 4–6. The conversion of the cyclopentenone (21) to the compound (28) is carried out as shown in flowchart A.

An additional novel route to the cyclopentenone alkynoates of this invention is shown in the following flowchart E, wherein n and y are as hereinabove defined.

In accordance with flowchart E, the ether (17) of flowchart A is reacted in Step A'''' with an alkali metal amide followed by a chloroalkyl bromide or iodide of formula (39) in liquid ammonia with tetrahydrofuran cosolvent. The product chloride of formula (40) is reacted in step B with an alkali metal cyanide in a suitable solvent, preferably hexamethylphosphoramide, to provide the corresponding nitrile of formula (41). Hydrolysis of the nitrile is accomplished with an alkali metal hydroxide, preferably sodium hydroxide, in a suitable solvent, for example, water or aqueous ethanol. The conversion of the product acid (42) to the compound (28) is carried out as shown in flowchart A for compound (20), where $R_5$ is hydrogen.

FLOWCHART E

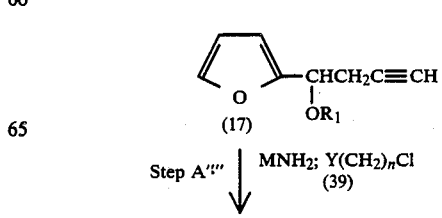

-continued
FLOWCHART E

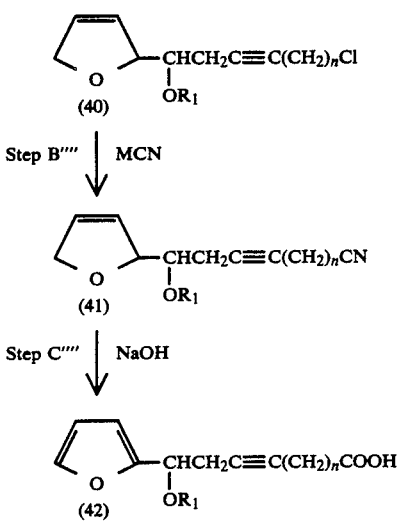

The invention will be described in greater detail in conjunction with the following examples.

EXAMPLE 1

4-(2-Furyl)-4-methoxy-1-butyne

To a stirred solution of propargyl aluminum bromide, prepared from 52.9 g of 80% propargyl bromide in toluene, 6.41 g of aluminum splutters activated with 70 mg of mercuric chloride and 80 ml of tetrahydrofuran, was added dropwise a solution of 42.2 g of furfural dimethyl acetal [J. Org. Chem., 40, 1478 (1975)] in 30 ml of tetrahydrofuran during a 15 minute period while maintaining a temperature of. 25° to 30° C. The mixture was stirred for 20 minutes at 25° C., then partitioned with ether and ice-water. The organic layer was separated, washed with water, then aqueous sodium bicarbonate, finally with brine and dried. After evaporation the residue was distilled, giving 39.8 g of the desired compound, bp 68°-69° C. (11 mm).

EXAMPLE 2

Methyl 8-(2-furyl)-8-methoxy-5-octynoate

To a stirred solution of 4.09 g of lithium amide and 200 ml of liquid ammonia was added dropwise a solution of 24.3 g of 4-(2-furyl)-4-methoxy-1-butyne in 20 ml of tetrahydrofuran during 10 minutes. The mixture was stirred under reflux for 30 minutes and then treated dropwise with a solution of 40.4 g of 1-bromo-4,4,4-trimethoxybutane (U.S. Pat. No. 3,864,387) in 40 ml of tetrahydrofuran during 10 minutes. This solution was stirred under reflux for 60 minutes, the ammonia was allowed to evaporate over one hour and the resulting solution stirred at 20° C. for 10 minutes. The solution was then partitioned between ether and water, the organic layer separated, washed with brine, dried and concentrated, giving 58 g of crude 8-(2-furyl)-1,1,1,8-tetramethoxy-5-octyne as a liquid.

This liquid was dissolved in 160 ml of methanol and the solution was treated with 3.2 ml of 4 N hydrochloric acid at 25° C. After 20 minutes the solution was treated with sodium bicarbonate solution and concentrated. The residue was extracted with ether. The extract was washed with brine, dried and concentrated. The residue was distilled at 0.08 mm on a Kugelrohr at 110°-120° C., giving 31.8 g of the desired compound as a colorless liquid.

EXAMPLE 3

8-(2-Furyl)-8-methoxy-5-octynoic acid

A solution of 1.25 g of methyl 8-(2-furyl)-8-methoxy-5-octynoate, 0.66 g of 85% potassium hydroxide, 15 ml of methanol and 10 ml of water was heated under reflux for one hour. The methanol was evaporated and the residue partitioned with ether and water. The aqueous layer was chilled at 0° to 10° C., acidified with hydrochloric acid and the product extracted with ether. The extract was washed with brine, dried and concentrated, giving 1.13 g of the desired compound as a colorless oil. The identification is established by PMR; $\delta$ 3.35 (3H, s, methyl ether).

EXAMPLE 4

Methyl 8-(2-Furyl)-8-hydroxy-5-octynoate

To a stirred solution of 16.3 g of 4-(2-furyl)-4-hydroxy-1-butyne [Ann. Chem. 682, 62 (1965)] in 120 ml of tetrahydrofuran was added 150 ml of a 1.6 M solution of n-butyllithium in hexane, during 30 minutes at 0° to 10° C. After 15 minutes at 0° to 10° C., the stirred solution was treated dropwise with a solution of 30 g of 1-bromo-4,4,4trimethoxybutane in 90 ml of hexamethylphosphoric triamide during 20 minutes while maintaining a temperature of −10° to 0° C. The mixture was warmed to 25° C., stirred for 18 hours, then poured into ice water and the crude product extracted with ether.

The extract, which contained 8-(2-furyl)-8-hydroxy-1,1,1-trimethoxy-5-octyne, was thoroughly washed with water and then stirred vigorously with 150 ml of 0.25 N hydrochloric acid at 10° to 15° C. for 15 minutes. The mixture was then treated with 100 ml of saturated sodium bicarbonate and the organic layer separated, washed with brine, dried and concentrated. The residue was distilled at 0.09 mm on a Kugelrohr at 145°-150° C., giving 15.8 g of the desired compound as an oil.

EXAMPLE 5

8-(2-Furyl)-8-hydroxy-5-octynoic acid

To a stirred solution of 4.73 g of methyl 8-(2-furyl)-8-hydroxy-5-octynoate in 60 ml of methanol was added 4 ml of 1 N potassium hydroxide. This mixture was stirred at reflux for one hour, then cooled and concentrated. The residue was partitioned between water and ether. The aqueous layer was separated, cooled to 0° C. and acidified with 1 N hydrochloric acid, then saturated with sodium chloride and extracted with ether. The ether extract was washed with brine, dried and concentrated, giving 4.39 g of the desired compound as an oil; PMR $\delta$ 4.85 (1H, t, CHOH).

EXAMPLE 6

7-(4-Hydroxycyclopent-2-en-1-on-2-yl)-5-heptynoic acid

A stirred solution of 25.0 g of methyl 8-(2-furyl)-8-methoxy-5-octynoate, 5.52 g of sodium dihydrogen phosphate monohydrate, 45.6 g of 86% phosphoric acid, 300 ml of dioxane and 200 ml of water was heated under reflux for 44 hours. The resulting solution, which contained a mixture of the 3- and 4-hydroxy isomers, was cooled to 50° C. and treated dropwise with 15 ml of concentrated sulfuric acid. This solution was stirred under reflux for 12 hours, cooled and partitioned with brine and ether. The organic layer was separated, washed with brine, dried and concentrated. The resulting oil was chromatographed on a silica gel column with chloroform progressively enriched in ether. The appropriate fractions were combined and concentrated, giving 6.4 g of the desired product which was recrystallized from ether, giving tan crystals, mp 65°–71° C.

EXAMPLE 7

2,5-Dihydro-2,5-dimethoxy-2-(3-butynyl)furan

To a stirred mixture of 6.01 g of 4-(2-furyl)-1-butyne [Perfumery Essent. Oil Reciord., 57, 364 (1966)], 10.6 g of sodium carbonate and 150 ml of methanol at −25° C., was added dropwise a solution of 8.0 g of bromine in 50 ml of methanol during a period of 3 hours. The mixture was then stirred at 25° C. for 45 minutes and concentrated in vacuo. The residue was partitioned with ether and brine. The ether layer was separated, washed with brine, dried and concentrated. Distillation of the residue at 0.5mm gave 6.62 g of the desired compound as a light yellow liquid, bp 57°–61° C. (0.5 mm).

EXAMPLE 8

2,5-Dihydro-2,5-dimethoxy-2-(8,8,8-trimethoxy-3-octynyl)furan

To a stirred mixture of 0.51 g of lithium amide and ml of liquid ammonia was added dropwise a solution of 3.64 g of 2,5-dihydro-2,5-dimethoxy-2-(3-butynyl)furan in 2.5 ml of tetrahydrofuran during 5 minutes. The mixture was stirred under reflux for 30 minutes and then treated dropwise with a solution of 5.0 g of 1-bromo-4,4,4-trimethoxybutane (U.S. Pat. No. 3,864,387) in 5 ml of tetrahydrofuran during 5 minutes. This solution was stirred under reflux for one hour, the ammonia allowed to evaporate during one hour and the resulting solution stirred at 20° C. for 10 minutes. This solution was partitioned with ether and brine. The organic layer was dried, treated with 2 drops of pyridine, and then concentrated, giving 7.1 g of the desired compound as a light amber oil; PMR $\delta$ 5.9 (2H, m, vinyl hydrogens).

EXAMPLE 9

Trimethylsilyl 7-(4-trimethylsiloxycyclopent-2-en-1-on-2-yl)-5-heptynoate

A stirred mixture of 7.1 g of 2,5-dihydro-2,5-di-methoxy-2-(8,8,8-trimethoxy-3-octynyl)furan, 2.76 g of sodium dihydrogen phosphate monohydrate, 140 mg of disodium hydrogen phosphate, 60 ml of dioxane and 40 ml of water was boiled under reflux for 19 hours, then cooled to 50° C. and treated dropwise with 4.1 ml of concentrated sulfuric acid. The resulting solution was boiled under reflux for 12 hours, cooled and partitioned with ether and brine. The ether layer was separated, washed with brine, dried and concentrated, giving 5.0 g of crude 7-(4-hydroxycyclopent-2-en-1-on-2-yl)-5-heptynoic acid. This crude product was dissolved in 40 ml of pyridine and the stirred solution treated at 0° to 10° C. with 10.5 ml of hexamethyldisilizane followed by 6.3 ml of chlorotrimethylsilane. The resulting mixture was stirred at 25° C. for 3 hours and then concentrated to dryness at 30° C. The residue was extracted with hexane, the extract filtered through diatomaceous earth and concentrated. The residue was distilled at 0.11 mm on a Kugelrohr at 155°–170° C., giving 1.66 g of the desired compound as an oil.

EXAMPLE 10

Methyl 7-(4-hydroxycyclopent-2-en-1-on-2-yl)-5-heptynoate

A stirred mixture of 5.8 g of 7-(4-hydroxycyclopent-2-en-1-on-2-yl)-5-heptynoic acid, 3.95 g of potassium carbonate, 7.4 g of iodomethane and 52 ml of acetone was refluxed for 2.5 hours. Most of the acetone was evaporated and the residue was partitioned with water and ether. The ether layer was separated, washed with brine, dried and concentrated, giving 5.02 g of the desired compound as an oil; PMR $\delta$ 3.72 (3H, s, methyl ester).

EXAMPLE 11

Methyl 7-(4-trimethylsiloxycyclopent-2-en-1-on-2-yl)-5-heptynoate

To a stirred solution of 5.0 g of methyl 7-(4-hydroxycyclopent-2-en-1-on-2-yl)-5-heptynoate in 27 ml of pyridine was added successively 2.53 ml of hexamethyldisilizane and 0.76 ml of chlorotrimethylsilane while maintaining a temperature of 0° to 10° C. The mixture was then stirred at 25° C. for 2 hours and then all volatile materials were evaporated at 30° C. in vacuo. The residue was slurried with hexane and this solution was filtered through diatomaceous earth. The filtrate was evaporated and the residue distilled at 0.06 mm on a Kugelrohr, giving 4.79 g of the desired compound as a colorless oil, bp 135°–140° C.

EXAMPLE 12

Methyl 7-(4-trimethylsiloxycylopent-2-en-1-on-2-yl)-5-cis-heptenoate

A stirred solution of 1.54 g of methyl 7-(4-tri-methylsiloxycyclopent-2-en-1-on-2-yl)-5-heptynoate, 0.25 ml of synthetic quinoline, 7.5 ml of hexane and 2.5 ml of toluene was hydrogenated at 0° C. and atmospheric pressure in the presence of 50 mg of lead-poisoned palladium on calcium. carbonate (Lindlar catalyst) until hydrogen uptake nearly ceased (2.5 hours). The catalyst was removed by filtration and the filtrate was concentrated. The residue was distilled at 0.06mm on a Kugelrohr, giving 1.58 g of the desired compound as a colorless oil, bp 130°–135° C.

EXAMPLE 13

Methyl 9-oxo-11α,16-dihydroxy-16-vinylprosta-5-yn-13-transenoate

To a stirred solution of 6.44 g of 4-trimethyl-siloxy-4-vinyl-1-(tri-n-butylstannyl)-trans-1-octane [J. Med. Chem., 25, 492 (1982)] in 10 ml of tetrahydrofuran at −78° C. was added 6.25 ml of 1.6 M n-butyllithium in hexane during 5 minutes. The resulting solution was stirred at −40° C. for 2 hours. The stirred solution was recooled to −78° C. and a solution prepared from 1.57 g of copper pentyne, 4.36 ml of hexamethylphosphorous triamide and 25 ml of ether was added. This solution was stirred at −78° C. for one hour and then treated during 5 minutes with a solution of 1.54 g of methyl 7-(4-trimethylsiloxycyclopent-2-en-1-on-2-yl)-5-heptynoate in 5 ml of ether. This solution was stirred at −40° C. for one hour, then at −20° C. for 5 minutes, then recooled to −78° C. and quenched with a solution of 1.2 ml of acetic acid in 10 ml of ether. This mixture was poured into a stirred mixture of ammonium chloride, dilute hydrochloric acid and ether. The ether phase was separated and washed successively with dilute hydrochloric acid, dilute brine-saturated sodium bicarbonate and finally brine. The washed solution was dried and concentrated, giving 8.2 g of light yellow oil. This oil was stirred with a solution of 40 ml of acetic acid, 20 ml of tetrahydrofuran and 10 ml of water at 25° C. for one hour. The solvents were evaporated with the aid of toluene and the residue partitioned with heptane and methanol. The methanol phase was concentrated and the residue purified by dry column chromatography on silica gel with 3:1 ethyl acetate:heptane, giving the desired compound as an oil; PMR δ 3.70 (3H, s, methyl ester) and 4.13 (1H, q, CHOH).

EXAMPLE 14

Methyl 9-oxo-11α,16-dihydroxy-16-vinylprosta-5-cis-13-trans-dienoate

A stirred solution of 0.86 g of methyl 9-oxo-11, 16-dihydroxy-16-vinylprosta-5-yn-13-cis-enoate in 2.2 ml of hexane and 2.2 ml of toluene was treated with 0.11 ml of synthetic quinoline and 22 mg of palladium on calcium carbonate catalyst (lead-poisoned; Lindlar catalyst) under argon. Hydrogen gas at one atmosphere was introduced and the mixture was stirred at 40° C. until 50 ml of hydrogen had been absorbed. The catalyst was filtered off and the filtrate concentrated. The residue was subjected to dry column chromatography on silica gel with 3:1 ethyl acetate:heptane, giving the desired compound as an oil; PMR δ 5.55 (2H, m, cis-CH=CH).

EXAMPLES 15-17

Following the general procedure of Example 6, treatment of the furans in the following table with phosphoric acid followed by sulfuric acid provides the cyclopentenolone product of Example 6.

TABLE

| Example | Starting Material |
| --- | --- |
| 15 | 8-(2-furyl)-8-methoxy-5-octynoic acid |
| 16 | methyl 8-(2-furyl)-8-hydroxy-5-octynoate |
| 17 | 8-(2-furyl)-8-hydroxy-5-octynoic acid |

EXAMPLE 18

8-(2-Furyl)-8-hydroxy-5-octynoic acid

To a stirred solution of 2.80 g of 5-pentynoic acid [Chem. Abst., 59, 9782d (1963)] in 50 ml of hexamethylphosphorous triamide was added 31.2 ml of 1.6 M n-butyllithium in hexane during 20 minutes at 15° C. After the addition, the solution was stirred for 10 minutes, then cooled to 0° C. and treated with 2.75 g of 2-(2-furyl)oxirane [Zh. Organ. Khim., 1, 539 (1965)]. The solution was warmed to 25° C., stirred for 5 hours and then partitioned with ether and dilute hydrochloric acid at 0° C. The ether layer was separated, washed, dried and evaporated. The resulting oil was chromatographed on silica gel, giving 2.49 g of the desired compound as an oil; PMR δ 4.85 (1H, t, CHOH).

EXAMPLE 19

7-Chloro-1-(2-furyl)-1-methoxy-3-heptyne

To a stirred mixture of 0.51 g of lithium amide and 25 ml of liquid ammonia was added a solution of 3.0 g of 4-(2-furyl)-4-methoxy-1-butyne in 2.5 ml of tetrahydrofuran. The mixture was stirred under reflux for 30 minutes and then treated with a solution of 3.94 g of 1-bromo-3-chloropropane in 5 ml of tetrahydrofuran. This mixture was stirred under reflux for one hour, then the ammonia was allowed to evaporate and the residue partitioned with ether and water. The ether layer was separated and evaporated. The residue was distilled at 0.06 mm on a Kugelrohr, giving 3.07 g of the desired compound as an oil, bp 110°–120° C.

EXAMPLE 20

7-Cyano-1-(2-furyl)-1-methoxy-3-heptyne

A stirred mixture of 0.45 g of 7-chloro-1-(2-furyl)-1-methoxy-3-heptyne, 0.20 g of sodium cyanide, and 4.0 ml of hexamethylphosphoric triamide was maintained at 25° C. for 22 hours. The mixture was partitioned with water and 1:1 hexaneether. The organic layer was washed with water and brine, dried and concentrated. The resulting oil was distilled at 0.30 mm on a Kugelrohr at 105°–110° C., giving 0.38 g of the desired compound as an oil; PMR δ 2.36 (2H, t, CH$_2$CN).

EXAMPLE 21

8-(2-Furyl)-8-methoxy-5-octynoic acid

A stirred mixture of 0.22 g of 7-cyano-1-(2-furyl)-1-methoxy-3-heptyne and 5.0 ml of 2.5 N sodium hydroxide was refluxed for 5 hours. The resulting solution was cooled, extracted with ether, and acidified at 0° with hydrochloric acid. The resulting mixture was extracted with ether. The extract was washed with brine, dried and concentrated to give the desired acid as an oil; PMR δ 3.35 (3H, s, methylether) and 2.40 (2H, t, CH$_2$COOH).

What is claimed is:

1. A compound of the formula

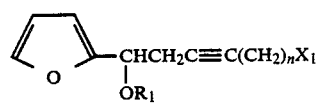

wherein R$_1$ is selected from the group consisting of hydrogen and C$_1$–C$_4$ alkyl; X$_1$ is selected from the group consisting of halogen, cyano, C$_1$–C$_4$ alkoxycarbonyl, carboxy and tri-(C$_1$–C$_4$alkoxy)methyl; and n is an integer 2–4 inclusive.

2. A compound of the formula

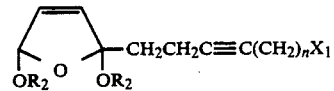

wherein R$_2$ is C$_1$–C$_4$ alkyl; X$_1$ is selected from the group consisting of halogen, cyano, C$_1$–C$_4$ alkoxycarbonyl, carboxy and tri-(C$_1$–C$_4$ alkoxy)methyl; and n is an integer 2–4 inclusive.

3. A compound according to claim 1 7-chloro-1-(2-furyl)-1-methoxy-3-heptyne.

4. A compound according to claim 1 7-cyano-1-(2-furyl)-1-methoxy-3-heptyne.

5. A compound according to claim 1 8-(2-furyl)-8-methoxy-5-octynoic acid.

6. A compound according to claim 1 methyl 8-(2-furyl)-8-methoxy-5-octynoate.

7. A compound according to claim 1 8-(2-furyl)-8-hydroxy-5-octynoic acid.

8. A compound according to claim 1 methyl 8-(2-furyl)-8-hydroxy-5-octynoate.

9. A compound 2,5-dihydro-2,5-dimethoxy-2-(8,8,8-trimethoxy-3-octynyl)furan.

* * * * *